US007582776B2

(12) United States Patent
Eckert et al.

(10) Patent No.: US 7,582,776 B2
(45) Date of Patent: Sep. 1, 2009

(54) PROCESS FOR PREPARING ARYLAMINOPROPANOLS

(75) Inventors: Markus Eckert, Shanghai (CN); Claus Dreisbach, Leichlingen (DE); Boris Bosch, Köln (DE); Andreas Stolle, Wuppertal (DE)

(73) Assignee: Lanxess Deutschland GmbH, Leverkusen (DE)

( * ) Notice: Subject to any disclaimer, the term of this patent is extended or adjusted under 35 U.S.C. 154(b) by 429 days.

(21) Appl. No.: 11/436,874

(22) Filed: May 18, 2006

(65) Prior Publication Data

US 2008/0262247 A1 Oct. 23, 2008

Related U.S. Application Data

(62) Division of application No. 10/391,348, filed on Mar. 18, 2003, now Pat. No. 7,169,938.

(30) Foreign Application Priority Data

Mar. 20, 2002 (DE) ................................ 102 12 301

(51) Int. Cl.
C07D 333/16 (2006.01)
(52) U.S. Cl. ...................................... 549/79
(58) Field of Classification Search .................. 549/72, 549/79
See application file for complete search history.

(56) References Cited

U.S. PATENT DOCUMENTS 5,362,886 A 11/1994 Berglund
2005/0107621 A1* 5/2005 Takehara et al. .............. 549/76

FOREIGN PATENT DOCUMENTS

| EP | 529 444 | 3/1993 |
| EP | 643 065 | 3/1995 |
| EP | 749 973 | 12/1996 |
| EP | 764 652 | 3/1997 |

OTHER PUBLICATIONS

Kumar Ashok, et al; "A new chemoenzymatic enantioselective synthesis of R-(–)-Tomoxetine, (R)- and (S)-fluoxetine"; Tetrahedron Letters, Elsevier Science Publishers, Amsterdam, NL, Bd. 32, Nr. 16, 1991; pp. 1901-1904; XPO02121769.
Ihuang, H.L. et al; "The synthesis of a J chiral fluoxetine intermediate by catalytic enantioselective hydrogenationof benzoylacetamide"; Tetrahedron: Asymmetry, Bd. 9, 1998, pp. 1637-1640; XPO02240972.
Sakuraba S. et al; "Efficient asymmetric I hydtogenation of Beta- and Gamma- amino ketone derivatives leading to practical synthesis of fluoxetine and eprozinol"; Chemical and pharmaceutical Bulletin; Pharmaceutical Society of Japan, Tokyo; Bd. 43, Nr. 5, 1995; XPO01071298; pp. 748-749.
Deeter J. et al; "Asymmetric synthesis and 118 absolute tereochemistry of Ly248686"; Tetrahedron Letters, Elsevier Science Publishers, Amsterdam, NL, Bd. 31, Nr. 49, Nov. 26, 1990; pp. 7101-7104, XP001119089.
Liu H. et al; "Chemo-enzymatic synthesis of the antidepressant duloxetine and its enantiomer"; Chirality, Wiley-Liss, New York, US Bd. 12, Nr. 1; 2000, pp. 26-29; XPO090003161.
Liu H., et al; "Chemoenzymatic synthesis of the non-tricyclic antidepressants fluoxetine, tomoxetine and nisoxetine"; J. Chem Soc., Perkin Trans. 1; 2000; pp. 1767-1769, XPO02240973.
Everaere, K. et al; "Steric effects in the enentioselective transfer hydrogenation of 2-roylacetates"; Tetrahedron: Asymmetry, Bd. 10, 1999; pp. 4663-4666; XPO02240974.
Boger D. L. et al; "Total synthesis of bleomycin A2 and related agents. 2. synthesis of (–)-pyrimidoblamic acid, epi-(+)-pyrimidoblamic acid, (+)-desacetamidopyrimidoblamic acid, and (–)-desacetamidopyrimidoblamic acid"; J. Am. Chem. Soc., Bd. 116, Nr. 13, 1994; pp. 5619-5630; XPO02240975.
Noyori, R. et al;"Ruthenium(II)-catalyzed asymmetric transfer hydrogenation of ketones using a formic acid- triethylamine mixture"; J. Am. Chem. Soc., Bd. 118, Nr. 10, 1996; pp. 2521-2522; XPO02240976.
Noyori, R. et al; J. Am. Chem. Soc. Supporting information, Bd. 118, 1996; pp. 1-39; XPO02240977.
Corey, E.J. et al; "Enantioselective and practical synthesis of R-and S-fluoxetines"; Tetrahedron letters; vol. 30, No. 39, 1989; p. 5207.
Wheeler, W.J.; "An asymmetreic synthesis of duloxetine hydrochlotride, a mixed uptake inhibitor of serotonin and norepinephrine, and its C-14 labeled isomers"; J. Lab. Comp. Radiopharm, 36; 1995; pp. 213-223.
Kalinin A.V.; "Directed ortho metalation—cross coupling links, carbamoyl rendition of the Baker-Venkataraman rearrangement, regiospecific route to substitute 4-hydroxycoumarins"; Tetrahedron Letters;, 39; 1998; p. 4995.
Hendi, S.B. et al; "A new synthesis of ●-keto amides via a reaction of ketone lithium enolates with isocyanates"; Synth. Commun. 17, 1987; pp. 13-18.
Balakumar S., "Electron transfer reactions of iron (III)—polypyridyl complexes with organic sulphides"; Tetrahedron Letters, vol. 51, No. 16; 1995, p. 4801.
Ager D. et al; "Reductions of 1,3-dicarbonyl systems with ruthenium-biarylbisphosphine catalysts"; Tetrahedron Asymmetry Report, vol. 8, No. 20; 1997; p. 3327.
Büchel K.H et al; "Methoden der Organischen Chemie"; Houben-Weyl, 4$^{th}$ edition, vol. E5; 1985; pp. 941-1010.
Büchel K. H et al; "Methoden der Organischen Chemie"; Houben-Weyl, 4$^{th}$ edition, vol. E 16d; 1992; pp. 987-1003.
Quiros et al; "Enantioselective reduction of beta-keto amides by the fungus *Mortierella isabellina*"; Tetrahedron: Asymmetry, vol. 8(18), (1997); pp. 3035-3038.
Gao and Sharpless; "Asymmetric synthesis of both enantiomers of tomoxeting and fluoxetine. Selective reduction of 2,3-epoxycinnamyl alcohol with red-A1"; J. Org. Chem., 1988; pp. 4081-4084.
Steiner et al; "S-fluoxetine in the prophylaxis of migraine: a phase II double-blind randomized placebo-controlled study"; Cephalalgia, vol. 18(5), 1989; pp. 283-286.

* cited by examiner

*Primary Examiner*—Taofig A Solola
(74) *Attorney, Agent, or Firm*—Norris McLaughlin & Marcus, P.A.

(57) ABSTRACT

The invention relates to a process for preparing enantiomerically enriched aryl-aminopropanols and to their use and also to intermediates.

8 Claims, No Drawings

PROCESS FOR PREPARING ARYLAMINOPROPANOLS

This application is a division of U.S. Ser. No. 10/391,348, filed Mar. 18, 2003, now U.S. Pat. No. 7,169,938 now pending; which claims foreign priority of German Patent Application 102 12 301.2, filed Mar. 20, 2002.

BACKGROUND OF THE INVENTION

1. Field of the Invention

The invention relates to a process for preparing enantiomerically enriched aryl-aminopropanols and to their use and also to intermediates.

2. Description of Related Art

1-Aryl-3-aminopropan-1-ols have gained industrial significance in particular as intermediates for the preparation of pharmaceuticals. For example, some 1-aryl-3-aminopropan-1-ols serve as precursor substances for the preparation of serotonin or noradrenaline takeup inhibitors. In the case of some of these inhibitors, it could be proven that certain enantiomers are not only inactive or less active, but may also even exhibit undesired side effects (U.S. Pat. No. 5,104,899).

Corey and Reichard (Tetrahedron Letters, 39, 5207, 1989) describe a process for preparing S-fluoxetine in which, in an important step, 3-chloropropiophenone is asymmetrically reduced using a chiral borane to give S-3-chloro-1-phenyl-1-propanol.

After reaction with sodium iodide and methylamine, (S)-3-(methylamino)-1-phenylpropan-1-ol is then obtained which may then be reacted further to the end product. Disadvantages of this process are that expensive reagents have to be used, and that the overall yield is only 77 to 82%.

A process for preparing enantiomerically enriched (1S)-3-(methylamino)-1-(2-thiophen-yl)-1-propanol starting from 1-(2-thiophen-yl)-3-chloropropan-1-one is described in Chirality 2000, 12, 26-29. After the reduction to racemic 3-chloro-1-(2-thienyl)-1-propanol, the racemate is enzymatically separated and the (S)-enantiomer is further reacted with NaI and methylamine to give (S)-3-(methylamino)-1-(2-thiophen-yl)-propan-1-ol. This method has the disadvantage that enzymatic racemate separations can in principle only provide 50% of the desired enantiomer and the overall yield is therefore economically unacceptable.

A similar synthetic route is described in J. Lab. Comp. Radiopharm. 1995, 36, 213-223, in which 1-(2-thiophen-yl)-3-chloropropan-1-one is asymmetrically reduced with borane and an oxazaborolidine. The yield in this step is only 61%, which makes the overall process uneconomic.

There was therefore a need for an efficient and widely applicable process for preparing enantiomerically enriched arylaminopropanols which starts from reactants obtainable in a simple manner.

SUMMARY OF THE INVENTION

A process has now been found for preparing enantiomerically enriched compounds of the formula (I)

where
Ar is a substituted or unsubstituted aryl radical and
$R^1$ and $R^2$ are each independently hydrogen, $C_1$-$C_{20}$-alkyl, $C_4$-$C_{14}$-aryl or $C_5$-$C_{15}$-arylalkyl, or the two $R^1$ and $R^2$ radicals together are $C_3$-$C_{12}$-alkylene, characterized in that
a) compounds of the formula (II) are converted to enantiomerically enriched compounds of the formula (III) or compounds of the formula (IV) are converted to enantiomerically enriched compounds of the formula (V)

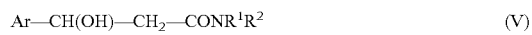

where, in each case,
Ar is as defined under the formula (I) and
$R^1$ and $R^2$ are each as defined under the formula (I) and
$R^3$ is hydrogen, $C_1$-$C_{20}$-alkyl, $C_4$-$C_{14}$-aryl or $C_5$-$C_{15}$-arylalkyl, and where the reaction is effected
in the presence of a transition metal catalyst
with hydrogen or a hydrogen-transferring compound or a mixture thereof and
b) in the case that compounds of the formula (II) have been used for step a), the enantiomerically enriched compounds of the formula (III) are reacted with amines of the formula (VI)

where $R^1$ and $R^2$ are each as defined under the formula (I) to give enantiomerically enriched compounds of the formula (V) as defined above and
c) the enantiomerically enriched compounds of the formula (V) are converted by reduction to enantiomerically enriched compounds of the formula (I) as defined above.

It is pointed out that the scope of the invention also encompasses any desired combinations of the ranges and areas of preference specified for each feature.

For the purposes of the invention, enantiomerically enriched refers to enantiomerically pure compounds or mixtures of enantiomers of a compound in which one enantiomer is present in an enantiomeric excess, also referred to hereinbelow as ee (enantiomeric excess), in comparison to the other enantiomer. This enantiomeric excess is preferably 10 to 100% ee, particularly preferably 60 to 100% ee and very particularly preferably 85 to 100% ee.

For the purposes of the invention, enantiomerically enriched relates in particular to the configuration of the carbon which is adjacent to the Ar radical.

DETAILED DESCRIPTION OF THE INVENTION

In the formulae (I) to (V), Ar is preferably a carbocyclic aromatic radical having 6 to 24 framework carbon atoms or a heteroaromatic radical having 4 to 24 framework carbon atoms in which no, one, two or three framework carbon atoms per cycle, but at least one framework carbon atom in the entire heteroaromatic radical, may be substituted by heteroatoms selected from the group of nitrogen, sulphur or oxygen.

The carbocyclic aromatic radicals or heteroaromatic radicals may also be substituted by up to five identical or different substituents per cycle selected from the group of hydroxyl, fluoro, nitro, cyano, free or protected formyl, $C_1$-$C_{12}$-alkyl, $C_1$-$C_{12}$-haloalkyl, $C_5$-$C_{14}$-aryl, $C_6$-$C_{15}$-arylalkyl, —PO—[($C_1$-$C_8$)-alkyl]$_2$, —PO—[($C_5$-$C_{14}$)-aryl]$_2$, —PO—[($C_1$-$C_8$)-alkyl)($C_5$-$C_{14}$)-aryl)], tri($C_1$-$C_8$-alkyl)siloxyl or a radical of the general formula (VII)

where, each independently,

A is missing or is a $C_1$-$C_8$-alkylene radical and

B is missing or is oxygen, sulphur or $NR^4$,
where $R^4$ is hydrogen, $C_1$-$C_8$-alkyl, $C_6$-$C_{15}$-arylalkyl or $C_5$-$C_{14}$-aryl and D is a carbonyl group and E is $R^5$, $OR^5$, $NHR^6$ or $N(R^6)_2$,
where $R^5$ is $C_1$-$C_8$-alkyl, $C_6$-$C_{15}$-arylalkyl, $C_1$-$C_8$-haloalkyl or $C_5$-$C_{14}$-aryl and
$R^6$ is in each case independently $C_1$-$C_8$-alkyl, $C_6$-$C_{15}$-arylalkyl or $C_6$-$C_{14}$-aryl, or $N(R^6)_2$ together is a cyclic amino radical, or a radical of the general formulae (VIIIa-e)

| A-E | (VIIIa) |
| A-$SO_2$-E | (VIIIb) |
| A-B-$SO_2R^2$ | (VIIIc) |
| A-$SO_3$W | (VIIId) |
| A-COW | (VIIIe) | where A, B, E and $R^2$ are each as defined above and W is OH, $NH_2$ or OM where M is an alkali metal ion, half an equivalent of an alkaline earth metal ion, an ammonium ion or an organic ammonium ion.

Particularly preferably, in the formulae (I) to (V) Ar is a monocyclic or bicyclic carbocyclic aromatic radical having a total of 6 to 14 framework carbon atoms or a mono- or bicyclic heteroaromatic radical having 4 to 12 framework carbon atoms in which no, one, two or three framework carbon atoms per cycle, but at least one framework carbon atom in the entire heteroaromatic radical, may be substituted by heteroatoms selected from the group of nitrogen, sulphur or oxygen, and where the mono- or bicyclic aromatic radical may be substituted by no, one, two or three radicals per cycle, each of which is independently selected from the group of hydroxyl, $C_1$-$C_{12}$-alkyl, cyano, COOH, COOM, COO—($C_1$-$C_{12}$-alkyl), COO—($C_4$-$C_{10}$-aryl), CO—($C_1$-$C_{12}$-alkyl), CO—($C_4$-$C_{10}$-aryl), O—($C_1$-$C_{12}$-alkyl), ($C_1$-$C_{12}$-alkyl)-O—($C_1$-$C_{12}$-alkyl), ($C_4$-$C_{10}$-aryl)-O—($C_1$-$C_{12}$-alkyl), O—($C_4$-$C_{10}$-aryl), O—CO—($C_4$-$C_{10}$-aryl), O—CO—($C_1$-$C_{12}$-alkyl), OCOO—($C_1$-$C_{12}$-alkyl), N—($C_1$-$C_{12}$-alkyl)$_2$, NH—($C_1$-$C_{12}$-alkyl), N($C_4$-$C_{10}$-aryl)$_2$, NH—($C_4$-$C_{10}$-aryl), fluorine, chlorine, bromine, $NO_2$, $SO_3H$, $SO_3M$, $SO_2(C_1$-$C_{12}$-alkyl), $SO(C_1$-$C_{12}$-alkyl), $C_1$-$C_{12}$-fluoroalkyl where fluoroalkyl is a singly, multiply or fully fluorine-substituted alkyl radical as defined above, NHCO—($C_1$-$C_{12}$-alkyl), $CONH_2$, CONH—($C_1$-$C_{12}$-alkyl), NHCOO—($C_1$-$C_{12}$-alkyl), PO($C_4$-$C_{10}$-aryl)$_2$, PO($C_1$-$C_{12}$-alkyl)$_2$, $PO_3H_2$, $PO_3M_2$, $PO_3HM$, PO(O($C_1$-$C_{12}$-alkyl)$_2$ where M is in each case an alkali metal ion or half an equivalent of an alkaline earth metal ion.

Very particularly preferably, aryl is phenyl, 2- or 3-thiophenyl, 2- or 3-furanyl, 2- or 3-pyrrolyl, 3- or 4-pyrazolyl, 1-, 2-, or 4-thiazolyl, 1-, 2-, or 4-oxazolyl, 2-, 4- or 5-imidazolyl, 2-, 3-, or 4-pyridyl, 2- or 3-pyrazinyl, 2-, 4-, or 5-pyrimidyl, 3-, 4-, 5- or 6-pyridazinyl, 2- or 3-indolyl, 3-indazolyl, indazolyl, 2- or 3-benzofuranyl, 2- or 3-benzothiophen-yl, 2-, 3- or 4-quinolinyl, isoquinolinyl 2-, 4-, 6- or 7-pteridinyl or 2-, 3-, 4-, 5-, 6-, 8-, 9- or 10-phenanthrenyl where each of the radicals mentioned bears no, one or two radicals per cycle, each of which is independently selected from the group of $C_1$-$C_4$-alkyl, cyano, COO—($C_1$-$C_4$-alkyl), O—($C_1$-$C_4$-alkyl), N($C_1$-$C_4$-alkyl)$_2$, NH—($C_1$-$C_4$-alkyl), fluorine, chlorine, bromine or $C_1$-$C_4$-fluoroalkyl, for example trifluoromethyl, 2,2,2-trifluoroethyl or pentafluoroethyl.

Even greater preference is given to Ar being 2-thiophen-yl.

$R^1$ and $R^2$ in the formulae (I), (IV), (V) and (VI) are preferably each independently hydrogen, methyl, ethyl, isopropyl, phenyl or benzyl.

$NR^1R^2$ as a whole in the formulae (I), (IV) and (V) is particularly preferably methylamino, ethylamino and isopropylamino, and, in formula (VI), $HNR^1R^2$ is methylamine, ethylamine and isopropylamine.

$NR^1R^2$ as whole in the formulae (I), (IV) and (V) is very particularly preferably methylamino, and, in formula (VI), $HNR^1R^2$ is methylamine.

$R^3$ in the formulae (II) and (III) is in each case preferably hydrogen, methyl, ethyl, isopropyl, n-propyl, tert-butyl, n-butyl, isobutyl, phenyl or benzyl, although particular preference is given to methyl and ethyl, and very particular preference to methyl.

Preferred compounds of the formula (II) for the process according to the invention are:

methyl 3-oxo-3-(2-thienyl)propanoate, ethyl 3-oxo-3-(2-thienyl)propanoate, isopropyl 3-oxo-3-(2-thienyl)propanoate, tert-butyl 3-oxo-3-(2-thienyl)propanoate, 2-ethylhexyl 3-oxo-3-(2-thienyl)propanoate, methyl 3-oxo-3-(phenyl)propanoate, ethyl 3-oxo-3-(phenyl)propanoate, isopropyl 3-oxo-3-(phenyl)propanoate, tert-butyl 3-oxo-3-(phenyl)propanoate, 2-ethylhexyl 3-oxo-3-(phenyl)propanoate, methyl 3-oxo-3-(4-tolyl)propanoate, ethyl 3-oxo-3-(4-tolyl)propanoate, isopropyl 3-oxo-3-(4-tolyl)propanoate, tert-butyl 3-oxo-3-(4-tolyl)propanoate and 2-ethylhexyl 3-oxo-3-(4-tolyl)propanoate.

Preferred compounds of the formula (IV) for the process according to the invention are:

3-oxo-3-(phenyl)propanamide, N-methyl-3-oxo-3-(phenyl)propanamide, N-benzyl-3-oxo-3-(phenyl)propanamide, N,N-dimethyl-3-oxo-3-(phenyl)propanamide, 3-oxo-3-(4-tolyl)propanamide, N-methyl-3-oxo-3-(4-tolyl)propanamide, N-benzyl-3-oxo-3-(4-tolyl)propanamide, N,N-dimethyl-3-oxo-3-(4-tolyl)propanamide, 3-oxo-3-(2-thienyl)propanamide, N-methyl-3-oxo-3-(2-thienyl)propanamide and N-benzyl-3-oxo-3-(2-thienyl)propanamide.

For the process according to the invention, preference is given to using compounds of the formula (II) in step a) having the definitions and areas of preference specified above.

For the process according to the invention, particular preference is given to using compounds of the formula (II) in step a) having the definitions and areas of preference specified above for Ar and $R^1$ and, in step b), to reacting with methylamine.

The compounds of the formula (II) which can be used for the process according to the invention may be obtained, for example, by reacting compounds of the formula (IX)

$$Ar—CO—CH_3 \quad (IX)$$

where Ar has the same definition and areas of preference specified under the formula (I)

with compounds of the formula (X)

$$R^3—O—CO—OR^3 \quad (X)$$

where the $R^3$ radicals each independently have the same definition and areas of preference as stated under the formula (II).

An example is the reaction of 2-acetylthiophene with dimethyl carbonate, diethyl carbonate, diphenyl carbonate or dibenzyl carbonate.

The compounds of the formula (IV) which can be used for the process according to the invention may be obtained in a similar manner to the compounds of the formula (II), for example, by base-catalysed reaction of compounds of the formula (IX) with compounds of the formula (XI)

$$R^3\text{—}O\text{—}CO\text{—}NR^1R^2 \quad (XI)$$

where $R^1$, $R^2$ and $R^3$ radicals each independently, but preferably identically, have the same definition and areas of preference as stated under the formulae (II) and (IV).

Examples of compounds of the formula (XI) include:

methyl N-methylcarbamate, ethyl N-methylcarbamate, methyl N-methylcarbamate, ethyl N-methylcarbamate, methyl N,N-dimethylcarbamate and ethyl N,N-dimethyl-carbamate.

Such a reaction is described, for example, in Tetrahedron Lett. 1998, 39, 4995 and may, for example, be applied in a similar manner for the reaction of 2-acetylthiophene with methyl N-methylcarbamate or ethyl N-methylcarbamate.

The compounds of the formula (IV) which can be used for the process according to the invention may likewise be obtained via a base-catalysed reaction of the compounds of the general formula (IX) with isocyanates, as described in Synth. Commun. 1987, 17, 13-18. An example is the reaction of 2-acetylthiophene with methyl isocyanate, ethyl isocyanate or benzyl isocyanate.

For the purposes of the invention, aryl is, for example and with preference, a carbocyclic aromatic radical or heteroaromatic radical which contains no, one, two or three heteroatoms per cycle, but at least one heteroatom in the entire heteroaromatic radical, which are selected from the group of nitrogen, sulphur or oxygen. The carbocyclic aromatic radicals or heteroaromatic radicals may also be substituted by up to five substituents per cycle, each of which is independently, for example and with preference, selected from the group of hydroxyl, $C_1$-$C_{12}$-alkyl, cyano, COOH, COOM where M is an alkali metal ion or half an equivalent of an alkaline earth metal ion, COO—($C_1$-$C_{12}$-alkyl), COO—($C_4$-$C_{10}$-aryl), CO—($C_1$-$C_{12}$-alkyl), CO—($C_4$-$C_{10}$-aryl), O—($C_1$-$C_{12}$-alkyl), O—($C_4$-$C_{10}$-aryl), N($C_1$-$C_{12}$-alkyl)$_2$, NH—($C_1$-$C_{12}$-alkyl), fluorine, chlorine, bromine, $C_1$-$C_{12}$-fluoroalkyl where fluoroalkyl is a singly, multiply or fully fluorine-substituted alkyl radical as defined above, CONH$_2$, CONH—($C_1$-$C_{12}$-alkyl), NHCOO—($C_1$-$C_{12}$-alkyl). The same applies to the aryl moiety of an arylalkyl radical.

For the purposes of the invention, alkyl or alkylene or alkoxy is in each case independently a straight-chain, cyclic, branched or unbranched alkyl or alkylene or alkoxy radical which may optionally be further substituted by $C_1$-$C_4$-alkoxy radicals. The same applies to the alkylene moiety of an arylalkyl radical.

In all contexts, $C_1$-$C_6$-alkyl is, for example, methyl, ethyl, n-propyl, isopropyl, n-butyl, tert-butyl, n-pentyl, cyclohexyl and n-hexyl, $C_1$-$C_8$-alkyl is additionally, for example, n-heptyl, n-octyl or isooctyl, $C_1$-$C_{12}$-alkyl is further additionally, for example, n-decyl and n-dodecyl, and $C_1$-$C_{20}$-alkyl is still further additionally n-hexadecyl and n-octadecyl.

For example, $C_1$-$C_4$-alkylene in all contexts is preferably methylene, 1,1-ethylene, 1,2-ethylene, 1,1-propylene, 1,2-propylene, 1,3-propylene, 1,1-butylene, 1,2-butylene, 2,3-butylene and 1,4-butylene, and $C_1$-$C_8$-alkylene is additionally 1,5-pentylene, 1,6-hexylene, 1,1-cyclohexylene, 1,4-cyclohexylene, 1,2-cyclohexylene and 1,8-octylene.

For example, $C_1$-$C_4$-alkoxy in all contexts is preferably methoxy, ethoxy, isopropoxy, n-propoxy, n-butoxy and tert-butoxy, and $C_1$-$C_8$-alkoxy is additionally cyclohexyloxy. The general term aryl as a substituent encompasses carbocyclic radicals and heteroaromatic radicals in which no, one, two or three framework atoms per cycle, but at least one framework atom in the entire radical, are heteroatoms selected from the group of nitrogen, sulphur or oxygen. $C_5$-$C_{10}$-Aryl is, for example and with preference, phenyl, pyridyl, o-, m- or p-tolyl, and $C_5$-$C_{14}$-aryl is additionally anthracenyl.

The same applies to the aryl moiety of an arylalkyl radical. $C_6$-$C_{15}$-Arylalkyl is, for example and with preference, benzyl.

For the purposes of the invention, haloalkyl and fluoroalkyl are each independently a straight-chain, cyclic, branched or unbranched alkyl radical which may be substituted by one or more, or fully by, halogen atoms independently selected from the group of fluorine, chlorine or bromine, and fluorine respectively.

For example and with preference, $C_1$-$C_8$-haloalkyl is in all contexts preferably trifluoromethyl, trichloromethyl, 2,2,2-trifluoroethyl, pentafluoroethyl and nonafluorobutyl and $C_1$-$C_8$-fluoroalkyl is trifluoromethyl, 2,2,2-trifluoroethyl, pentafluoroethyl and nonafluorobutyl.

Protected formyl means a formyl radical which is protected by converting to aminal, acetal or a mixed aminalacetal where the aminals, acetals and mixed aminalacetals may be acyclic or cyclic.

For example and with preference, protected formyl is a 1,1-(2,5-dioxy)cyclopentylene radical.

In step a) of the process according to the invention, the compounds of the formula (II) are converted in the presence of a transition metal catalyst to enantiomerically enriched compounds of the formula (III), or compounds of the formula (IV) are converted to enantiomerically enriched compounds of the formula (V), and the reaction is effected with hydrogen or a hydrogen-transferring compound or a mixture thereof.

The catalytic reduction of ketones to enantiomerically enriched secondary alcohols is known in principle. The reducing agents used are customarily molecular hydrogen or, in the case of transfer hydrogenations, hydrogen-transferring compounds, for example formic acid or isopropanol.

Step a) may be carried out, for example and with preference, in such a way that the compounds of the formula (II) or the compounds of the formula (IV) are reduced by hydrogen in the presence of transition metal catalysts and optionally solvents which comprise chiral, stereoisomerically enriched ruthenium, rhodium, iridium or palladium complexes, or are obtained by reacting ruthenium, rhodium, iridium or palladium salts with stereoisomerically enriched ligands.

For example, the asymmetric hydrogenation of aryl β-ketoesters using Ru-phosphine catalysts is described in Tetrahedron 1995, 27, 4801 or Org. and Organomet. Synth. 1999, 2, 175. An overview article can be found in Tetrahedron Asymmetry 1997, 8, 3327. Ruthenium catalysts having binaphthyl or biphenylphosphine ligands are suitable in particular for the asymmetric hydrogenation, as described in EP 529444, EP 643 065, EP 749 973 and EP 764 652.

However, for the process according to the invention, preference is given to carrying out step a) as a transfer hydrogenation.

In a preferred embodiment, step a) is carried out in such a way that the compounds of the formula (II) or the compounds of the formula (IV) are reacted i) in the presence of a ruthenium-, rhodium- or iridium-containing catalyst and
ii) in the presence of at least one amine, at least some of which is present in protonated form,
iii) with formic acid, formate or mixtures thereof.
iv) optionally in the presence of organic solvent.

For example and with preference, the catalysts used are those which comprise ruthenium complexes. Preferred ruthenium complexes are those which are obtainable by reacting compounds of the formula (XII) with compounds of the formula (XIII), or complexes of the formula (XIV). Particular preference is given to using those ruthenium complexes which are obtainable by reacting compounds of the formula (XII) with compounds of the formula (XIII). In a preferred embodiment, the molar ratio of compounds of the formula (XIII) to compounds of the formula (II) is 2:1 to 3:1, particularly preferably 2.01:1 to 2.4:1.

Advantageously, compounds of the formula (XIII) and compounds of the formula (XII) are mixed and the mixture is taken up in organic solvent. The resulting mixture may also, before addition to the reaction mixture, advantageously be stirred with a base, preferably a tertiary amine and, for example and with preference, for 10 to 30 min, and the molar amount of tertiary amine is, for example and with preference, 1:1 to 3:1, more preferably 1:1 to 2:1, based on compounds of the formula (XIII).

For organic solvents and amines, the same statements and areas of preference apply as will be described in detail below.

In the compounds of the formula (XII)

$$[RuX_2(arene)]_2 \quad (XII),$$

arene is a coordinated aromatic compound having 6 to 12 ring carbon atoms which may be further substituted by up to 6 radicals, each of which is independently selected from the group of $C_1$-$C_8$-alkyl, benzyl and phenyl and X is, for example and with preference, chlorine, bromine or iodine, particularly preferably chlorine.

Arene is preferably benzene or naphthalene which may be substituted by up to 6 radicals, each of which is independently selected from the group of methyl, ethyl, n-propyl, isopropyl and tert-butyl.

Arene is preferably mesitylene, cumene or benzene.

Particularly preferred compounds of the formula (XII) are:

(benzene)dichlororuthenium dimer, (mesitylene)dichlororuthenium dimer and (cumene)dichlororuthenium dimer, and even greater preference is given to (cumene)dichlororuthenium dimer.

In the formula (XIII)

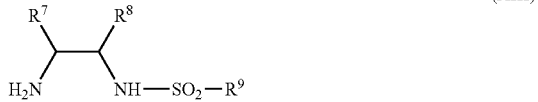

(XIII)

$R^7$ and $R^8$ are each independently, for example, $C_1$-$C_{20}$-alkyl, $C_4$-$C_{15}$-aryl or $C_5$-$C_{16}$-arylalkyl, or $R^7$ and $R^8$ together are a straight-chain or branched $C_3$-$C_{12}$-alkylene radical, and $R^9$ is $C_1$-$C_{20}$-alkyl, $C_1$-$C_{20}$-fluoroalkyl or $C_4$-$C_{15}$-aryl.

$R^7$ and $R^8$ are preferably identically phenyl or are together straight-chain $C_3$-$C_8$-alkylene, for example 1,3-propylene or 1,4-butylene, and $R^7$ and $R^8$ are particularly preferably identically phenyl.

$R^9$ is preferably $C_1$-$C_4$-alkyl, $C_1$-$C_4$-fluoroalkyl, phenyl or naphthyl which may be further substituted by no, one, two, three, four or five radicals which are selected from the group of $C_1$-$C_4$-alkyl, $C_1$-$C_4$-alkoxy, $C_1$-$C_4$-fluoroalkyl, fluorine and chlorine.

$R^9$ is particularly preferably methyl, trifluoromethyl, pentafluoroethyl, nonafluorobutyl, phenyl, p-tolyl, p-ethylphenyl, p-anisyl, p-ethoxyphenyl, p-chlorophenyl, 2,4,6-trimethylphenyl, 2,4,6-triisopropylphenyl, p-fluorophenyl, pentafluorophenyl and naphthyl.

$R^9$ is very particularly preferably p-tolyl, phenyl, naphthyl.

$R^9$ is even more preferably p-tolyl.

The compounds of the formula (XIII) preferably had a stereoisomeric purity of 90% or more, particularly preferably 95% or more and very particularly preferably 98.5% or more.

Examples of compounds of the formula (XIII) include:

N-[(1R,2R) and (1S,2S)-2-amino-1,2-diphenylethyl]-p-tolylsulphonamide, N[(1R,2R) and (1S,2S)-2-amino-1,2-diphenylethyl]-o-tolylsulphonamide, N-[(1R,2R) and (1S,2S)-2-amino-1,2-diphenylethyl]-m-tolylsulphonamide, N-[(1R,2R) and (1S,2S)-2-amino-1,2-diphenylethyl]-phenylsulphonamide, N-[(1R,2R) and (1S,2S)-2-amino-1,2-diphenylethyl]-4-ethylphenylsulphonamide, N-[(1R,2R) and (1S,2S)-2-amino-1,2-diphenylethyl]-3-ethylphenylsulphonamide, N-[(1R,2R) and (1S,2S)-2-amino-1,2-diphenylethyl]-2-ethylphenylsulphonamide, N-[(1R,2R) and (1S,2S)-2-amino-1,2-diphenylethyl]-2,4,6-trimethylphenylsulphonamide, N-[(1R,2R) and (1S,2S)-2-amino-1,2-diphenylethyl]-2,4,6-triisopropylphenylsulphonamide, N-[(1R,2R) and (1S,2S)-2-amino-1,2-diphenylethyl]-4-chlorophenylsulphonamide, N-[(1R,2R) and (1S,2S)-2-amino-1,2-diphenylethyl]-3-chlorophenylsulphonamide, N-[(1R,2R) and (1S,2S)-2-amino-1,2-diphenylethyl]-2-chlorophenylsulphonamide, N-[(1R,2R) and (1S,2S)-2-amino-1,2-diphenylethyl]-4-fluorophenylsulphonamide, N-[(1R,2R) and (1S,2S)-2-amino-1,2-diphenylethyl]-3-fluorophenylsulphonamide, N-[(1R,2R) and (1S,2S)-2-amino-1,2-diphenylethyl]-2-fluorophenylsulphonamide, N-[(1R,2R) and (1S,2S)-2-amino-1,2-diphenylethyl]-4-methoxyphenylsulphonamide, N-[(1R,2R) and (1S,2S)-2-amino-1,2-diphenylethyl]-3-methoxyphenylsulphonamide, N-[(1R,2R) and (1S,2S)-2-amino-1,2-diphenylethyl]-2-methoxyphenylsulphonamide, N-[(1R,2R) and (1S,2S)-2-amino-1,2-diphenylethyl]-1-naphthylsulphonamide, N-[(1R,2R) and (1S,2S)-2-amino-1,2-diphenylethyl]-2-naphthylsulphonamide, N-[(1R,2R) and (1S,2S)-2-amino-1,2-diphenylethyl]-pentafluorophenylsulphonamide, N-[(1R,2R) and (1S,2S)-2-amino-1,2-diphenylethyl]-methanesulphonamide, N-[(1R,2R) and (1S,2S)-2-amino-1,2-diphenylethyl]-trifluoromethanesulphonamide, N-[(1R,2R) and (1S,2S)-2-aminocyclohexyl]-p-tolylsulphonamide, N-[(1R,2R) and (1S,2S)-2-aminocyclohexyl]-o-tolylsulphonamide, N-[(1R,2R) and (1S,2S)-2-aminocyclohexyl]-m-tolylsulphonamide, N-[(1R,2R) and (1S,2S)-2-aminocyclohexyl]-phenylsulphonamide, N-[(1R,2R) and (1S,2S)-2-aminocyclohexyl]-4-ethylphenylsulphonamide, N-[(1R,2R) and (1S,2S)-2-aminocyclohexyl]-3-ethylphenylsulphonamide, N-[(1R,2R) and (1S,2S)-2-aminocyclohexyl]-2-ethylphenylsulphonamide, N-[(1R,2R) and (1S,2S)-2-aminocyclohexyl]-2,4,6-trimethylphenylsulphonamide, N-[(1R,2R) and (1S,2S)-2-aminocyclohexyl]-2,4,6-triisopropylphenylsulphonamide, N-[(1R,2R) and (1S,2S)-2-aminocyclohexyl]-4-chlorophenylsulphonamide, N-[(1R,2R) and (1S,2S)-2-aminocyclohexyl]-3-chlorophenylsulphonamide, N-[(1R,2R) and (1S,2S)-2-aminocyclohexyl]-2-chlorophenylsulphonamide, N-[(1R,2R) and (1S,2S)-2-aminocyclohexyl]-4-fluorophenylsulphonamide, N-[(1R,2R) and (1S,2S)-2-aminocyclohexyl]-3-fluorophenylsulphonamide, N-[(1R,2R) and (1S,2S)-2-aminocyclohexyl]-2-fluorophenylsulphonamide, N-[(1R,2R) and (1S,2S)-2-aminocyclohexyl]-4-methoxyphenylsulphonamide, N-[(1R,2R) and (1S,2S)-2-aminocyclohexyl]-3-methoxyphenylsulphonamide, N-[(1R,2R) and (1S,2S)-2-aminocyclohexyl]-2-methoxyphenylsulphonamide, N-[(1R,2R) and (1S,2S)-2-aminocyclohexyl]-1-naphthylsulphonamide, N-[(1R,2R) and (1S,2S)-2-aminocyclohexyl]-2-naphthylsulphonamide, N-[(1R,2R) and (1S,2S)-2-aminocyclohexyl]-pentafluorophenylsulphonamide, N-[(1R,2R) and (1S,2S)-2-aminocyclohexyl]-methanesulphonamide, N-[(1R,2R) and (1S,2S)-2-aminocyclohexyl]-trifluoromethanesulphonamide, N-[(1R,2R) and (1S,2S)-2-aminocyclopentyl]-p-tolylsulphonamide, N-[(1R,2R) and (1S,2S)-2-aminocyclopentyl]-o-tolylsulphonamide, N-[(1R,2R) and (1S,2S)-2-aminocyclopentyl]-m-tolylsulphonamide, N-[(1R,2R) and (1S,2S)-2-aminocyclopentyl]phenylsulphonamide, N-[(1R,2R) and (1S,2S)-2-aminocyclopentyl]-4-ethylphenylsulphonamide, N-[(1R,2R) and (1S,2S)-2-aminocyclopentyl]-3-ethylphenylsulphonamide, N-[(1R,2R) and (1S,2S)-2-aminocyclopentyl]-2-ethylphenylsulphonamide, N-[(1R,2R) and (1S,2S)-2-aminocyclopentyl]-2,4,6-trimethylphenylsulphonamide, N-[(1R,2R) and (1S,2S)-2-aminocyclopentyl]-2,4,6-triisopropylphenylsulphonamide, N-[(1R,2R) and (1S,2S)-2-aminocyclopentyl]-4-chlorophenylsulphonamide, N-[(1R,2R) and (1S,2S)-2-aminocyclopentyl]-3-chlorophenylsulphonamide, N-[(1R,2R) and (1S,2S)-2-aminocyclopentyl]-2-chlorophenylsulphonamide, N-[(1R,2R) and (1S,2S)-2-aminocyclopentyl]-4-fluorophenylsulphonamide, N-[(1R,2R) and (1S,2S)-2-aminocyclopentyl]-3-fluorophenylsulphonamide, N-[(1R,2R) and (1S,2S)-2-aminocyclopentyl]-2-fluorophenylsulphonamide, N-[(1R,2R) and (1S,2S)-2-aminocyclopentyl]-4-methoxyphenylsulphonamide, N-[(1R,2R) and (1S,2S)-2-aminocyclopentyl]-3-methoxyphenylsulphonamide, N-[(1R,2R) and (1S,2S)-2-aminocyclopentyl]-2-methoxyphenylsulphonamide, N-[(1R,2R) and (1S,2S)-2-aminocyclopentyl]-1-naphthylsulphonamide, N-[(1R,2R) and (1S,2S)-2-aminocyclopentyl]-2-naphthylsulphonamide, N-[(1R,2R) and (1S,2S)-2-aminocyclopentyl]-pentafluorophenylsulphonamide, N-[(1R,2R) and (1S,2S)-2-aminocyclopentyl]-methanesulphonamide, N-[(1R,2R) and (1S,2S)-2-aminocyclopentyl]-trifluoromethanesulphonamide.

In the formula (XIV)

$$[RuX_2(arene)\{(XIII)\}] \quad (XIV),$$

arene and X each have the definition and areas of preference specified under formula (XII), (XIII) in the formula (XIV) represents compounds of the formula (XIII) with the definitions and areas of preference specified there.

Compounds of the formula (XIV) include:

[N-[(1R,2R and 1S,2S)-2-(amino-κN)-1,2-diphenylethyl]-p-tolylsulphonamidato-κN]-chloro[(η$^6$)-cumene]ruthenium(II)

[N-[(1R,2R and 1S,2S)-2-(amino-κN)-1,2-diphenylethyl]-o-tolylsulphonamidato-κ]-chloro[(η$^6$)-cumene]ruthenium(II)

[N-[(1R,2R and 1S,2S)-2-(amino-κN)-1,2-diphenylethyl]-m-tolylsulphonamidato-κN]-chloro[(η$^6$)-cumene]ruthenium(II)

[N-[(1R,2R and 1S,2S)-2-(amino-κN)-1,2-diphenylethyl]-phenylsulphonamidato-κN]-chloro[(η$^6$)-cumene]ruthenium(II)

[N-[(1R,2R and 1S,2S)-2-(amino-κN)-1,2-diphenylethyl]-4-ethylphenylsulphonamidato-κN]chloro[(η$^6$)-cumene]ruthenium(II)

[N-[(1R,2R and 1S,2S)-2-(amino-κN)-1,2-diphenylethyl]-3-ethylphenylsulphonamidato-κN]chloro[(η$^6$)-cumene]ruthenium(II)

[N-[(1R,2R and 1S,2S)-2-(amino-κN)-1,2-diphenylethyl]-2-ethylphenylsulphonamidato-κN]chloro[(η$^6$)-cumene]ruthenium(II)

[N-[(1R,2R and 1S,2S)-2-(amino-κN)-1,2-diphenylethyl]-2,4,6-trimethylphenylsulphonamidato-κN]chloro[(η$^6$)-cumene]ruthenium(II)

[N-[(1R,2R and 1S,2S)-2-(amino-κN)-1,2-diphenylethyl]-2,4,6-triisopropylphenylsulphonamidato-κN]chloro[(η$^6$)-cumene]ruthenium(II)

[N-[(1R,2R and 1S,2S)-2-(amino-κN)-1,2-diphenylethyl]-4-chlorophenylsulphonamidato-κN]chloro[(η$^6$)-cumene]ruthenium(II)

[N-[(1R,2R and 1S,2S)-2-(amino-κN)-1,2-diphenylethyl]-3-chlorophenylsulphonamidato-κN]chloro[(η$^6$)-cumene]ruthenium(II)

[N-[(1R,2R and 1S,2S)-2-(amino-κN)-1,2-diphenylethyl]-2-chlorophenylsulphonamidato-κN]chloro[(η$^6$)-cumene]ruthenium(II)

[N-[(1R,2R and 1S,2S)-2-(amino-κN)-1,2-diphenylethyl]-4-fluorophenylsulphonamidato-κN]chloro[(η$^6$)-cumene]ruthenium(II)

[N-[(1R,2R and 1S,2S)-2-(amino-κN)-1,2-diphenylethyl]-3-fluorophenylsulphonamidato-κN]chloro[(η$^6$)-cumene]ruthenium(II)

[N-[(1R,2R and 1S,2S)-2-(amino-κN)-1,2-diphenylethyl]-2-fluorophenylsulphonamidato-κN]chloro[(η$^6$)-cumene]ruthenium(II)

[N-[(1R,2R and 1S,2S)-2-(amino-κN)-1,2-diphenylethyl]-4-methoxyphenylsulphonamidato-κN]chloro[(η$^6$)-cumene]ruthenium(II)

[N-[(1R,2R and 1S,2S)-2-(amino-κN)-1,2-diphenylethyl]-3-methoxyphenylsulphonamidato-κN]chloro[(η$^6$)-cumene]ruthenium(II)

[N-[(1R,2R and 1S,2S)-2-(amino-κN)-1,2-diphenylethyl]-2-methoxyphenylsulphonamidato-κN]chloro[(η$^6$)-cumene]ruthenium(II)ato-κN]chloro[(η$^6$)-cumene]ruthenium(II)

[N-[(1R,2R and 1S,2S)-2-(amino-κN)-1,2-diphenylethyl]-1-naphthylsulphonamidato-κN]chloro[(η$^6$)-cumene]ruthenium(II)

[N-[(1R,2R and 1S,2S)-2-(amino-κN)-1,2-diphenylethyl]-2-naphthylsulphonamidato-κN]chloro[(η$^6$)-cumene]ruthenium(II)

[N-[(1R,2R and 1S,2S)-2-(amino-κN)-1,2-diphenylethyl]-pentafluorophenylsulphonamidato-κN]chloro[(η$^6$)-cumene]ruthenium(II)

[N-[(1R,2R and 1S,2S)-2-(amino-κN)-1,2-diphenylethyl]-methanesulphonamidato-κN]chloro[(η$^6$)-cumene]ruthenium(II)

[N-[(1R,2R and 1S,2S)-2-(amino-κN)-1,2-diphenylethyl]-trifluoromethanesulphonamidato-κN]chloro[(η$^6$)-cumene]ruthenium(II)

[N-[(1R,2R and 1S,2S)-2-(amino-κN)-1,2-diphenylethyl]-p-tolylsulphonamidato-κN]-chloro[(η$^6$)-1,3,5-trimethylbenzene]ruthenium(II)

[N-[(1R,2R and 1S,2S)-2-(amino-κN)-1,2-diphenylethyl]-o-tolylsulphonamidato-κN]chloro[(η$^6$)-1,3,5-trimethylbenzene]ruthenium(II)

[N-[(1R,2R and 1S,2S)-2-(amino-κN)-1,2-diphenylethyl]-m-tolylsulphonamidato-κN]chloro[(η$^6$)-1,3,5-trimethylbenzene]ruthenium(II)

[N-[(1R,2R and 1S,2S)-2-(amino-κN)-1,2-diphenylethyl]-phenylsulphonamidato-κN]-chloro[(η$^6$)-1,3,5-trimethylbenzene]ruthenium(II)

[N-[(1R,2R and 1S,2S)-2-(amino-κN)-1,2-diphenylethyl]-4-ethylphenylsulphonamidato-κN]chloro[(η$^6$)-1,3,5-trimethylbenzene]ruthenium(II)

[N-[(1R,2R and 1S,2S)-2-(amino-κN)-1,2-diphenylethyl]-3-ethylphenylsulphonamidato-κN]chloro[(η¹⁶)-1,3,5-trimethylbenzene]ruthenium(II)

[N-[(1R,2R and 1S,2S)-2-(amino-κN)-1,2-diphenylethyl]-2-ethylphenylsulphonamidato-κN]chloro[($\eta^6$)-1,3,5-trimethylbenzene]ruthenium(II)

[N-[(1R,2R and 1S,2S)-2-(amino-κN)-1,2-diphenylethyl]-2,4,6-trimethylphenylsulphonamidato-κN]chloro[($\eta^6$)-1,3,5-trimethylbenzene]ruthenium(II)

[N-[(1R,2R and 1S,2S)-2-(amino-κN)-1,2-diphenylethyl]-2,4,6-triisopropylphenylsulphonamidato-κN]chloro[($\eta^6$)-1,3,5-trimethylbenzene]ruthenium(II)

[N-[(1R,2R and 1S,2S)-2-(amino-κN)-1,2-diphenylethyl]-4-chlorophenylsulphonamidato-κN]chloro[($\eta^6$)-1,3,5-trimethylbenzene]ruthenium(II)

[N-[(1R,2R and 1S,2S)-2-(amino-κN)-1,2-diphenylethyl]-3-chlorophenylsulphonamidato-κN]chloro[($\eta^6$)-1,3,5-trimethylbenzene]ruthenium(II)

[N-[(1R,2R and 1S,2S)-2-(amino-κN)-1,2-diphenylethyl]-2-chlorophenylsulphonamidato-κN]chloro[($\eta^6$)-1,3,5-trimethylbenzene]ruthenium(II)

[N-[(1R,2R and 1S,2S)-2-(amino-κN)-1,2-diphenylethyl]-4-fluorophenylsulphonamidato-κN]chloro[($\eta^6$)-1,3,5-trimethylbenzene]ruthenium(II)

[N-[(1R,2R and 1S,2S)-2-(amino-κN)-1,2-diphenylethyl]-3-fluorophenylsulphonamidato-κN]chloro[($\eta^6$)-1,3,5-trimethylbenzene]ruthenium(II)

[N-[(1R,2R and 1S,2S)-2-(amino-κN)-1,2-diphenylethyl]-2-fluorophenylsulphonamidato-κN]chloro[($\eta^6$)-1,3,5-trimethylbenzene]ruthenium(II)

[N-[(1R,2R and 1S,2S)-2-(amino-κN)-1,2-diphenylethyl]-4-methoxyphenylsulphonamidato-κN]chloro[($\eta^6$)-1,3,5-trimethylbenzene]ruthenium(II)

[N-[(1R,2R and 1S,2S)-2-(amino-κN)-1,2-diphenylethyl]-3-methoxyphenylsulphonamidato-κN]chloro[($\eta^6$)-1,3,5-trimethylbenzene]ruthenium(II)

[N-[(1R,2R and 1S,2S)-2-(amino-κN)-1,2-diphenylethyl]-2-methoxyphenylsulphonamidato-κN]chloro[($\eta^6$)-1,3,5-trimethylbenzene]ruthenium(II)ato-κN]chloro[($\eta^6$)-1,3,5-trimethylbenzene]ruthenium(II)

[N-[(1R,2R and 1S,2S)-2-(amino-κN)-1,2-diphenylethyl]-1-naphthylsulphonamidato-κN]chloro[($\eta^6$)-1,3,5-trimethylbenzene]ruthenium(II)

[N-[(1R,2R and 1S,2S)-2-(amino-κN)-1,2-diphenylethyl]-2-naphthylsulphonamidato-κN]chloro[($\eta^6$)-1,3,5-trimethylbenzene]ruthenium(II)

[N-[(1R,2R and 1S,2S)-2-(amino-κN)-1,2-diphenylethyl]-pentafluorophenylsulphonamidato-κN]chloro[($\eta^6$)-1,3,5-trimethylbenzene]ruthenium(II)

[N-[(1R,2R and 1S,2S)-2-(amino-κN)-1,2-diphenylethyl]-methanesulphonamidato-κN]-chloro[($\eta^6$)-1,3,5-trimethylbenzene]ruthenium(II)

[N-[(1R,2R and 1S,2S)-2-(amino-κN)-1,2-diphenylethyl]-trifluoromethanesulphonamidato-κN]chloro[($\eta^6$)-1,3,5-trimethylbenzene]ruthenium(II)

[N-[(1R,2R and 1S,2S)-2-(amino-κN)-1,2-diphenylethyl]-p-tolylsulphonamidato-κN]-chloro[($\eta^6$)-benzene]ruthenium(II)

[N-[(1R,2R and 1S,2S)-2-(amino-κN)-1,2-diphenylethyl]-o-tolylsulphonamidato-κN]chloro[($\eta^6$)-benzene]ruthenium(II)

[N-[(1R,2R and 1S,2S)-2-(amino-κN)-1,2-diphenylethyl]-m-tolylsulphonamidato-κN]-chloro[($\eta^6$)-benzene]ruthenium(II)

[N-[(1R,2R and 1S,2S)-2-(amino-κN)-1,2-diphenylethyl]-phenylsulphonamidato-κN]-chloro[($\eta^6$)-benzene]ruthenium(II)

[N-[(1R,2R and 1S,2S)-2-(amino-κN)-1,2-diphenylethyl]-4-ethylphenylsulphonamidato-κN]chloro[($\eta^6$)-benzene]ruthenium(II)

[N-[(1R,2R and 1S,2S)-2-(amino-κN)-1,2-diphenylethyl]-3-ethylphenylsulphonamidato-κN]chloro[($\eta^6$)-benzene]ruthenium(II)

[N-[(1R,2R and 1S,2S)-2-(amino-κN)-1,2-diphenylethyl]-2-ethylphenylsulphonamidato-κN]chloro[($\eta^6$)-benzene]ruthenium(II)

[N-[(1R,2R and 1S,2S)-2-(amino-κN)-1,2-diphenylethyl]-2,4,6-trimethylphenylsulphonamidato-κN]chloro[($\eta^6$)-benzene]ruthenium(II)

[N-[(1R,2R and 1S,2S)-2-(amino-κN)-1,2-diphenylethyl]-2,4,6-triisopropylphenylsulphonamidato-κN]chloro[($\eta^6$)-benzene]ruthenium(II)

[N-[(1R,2R and 1S,2S)-2-(amino-κN)-1,2-diphenylethyl]-4-chlorophenylsulphonamidato-κN]chloro[($\eta^6$)-benzene]ruthenium(II)

[N-[(1R,2R and 1S,2S)-2-(amino-κN)-1,2-diphenylethyl]-3-chlorophenylsulphonamidato-κN]chloro[($\eta^6$)-benzene]ruthenium(II)

[N-[(1R,2R and 1S,2S)-2-(amino-κN)-1,2-diphenylethyl]-2-chlorophenylsulphonamidato-κN]chloro[($\eta^6$)-benzene]ruthenium(II)

[N-[(1R,2R and 1S,2S)-2-(amino-κN)-1,2-diphenylethyl]-4-fluorophenylsulphonamidato-κN]chloro[($\eta^6$)-benzene]ruthenium(II)

[N-[(1R,2R and 1S,2S)-2-(amino-κN)-1,2-diphenylethyl]-3-fluorophenylsulphonamidato-κN]chloro[($\eta^6$)-benzene]ruthenium(II)

[N-[(1R,2R and 1S,2S)-2-(amino-κN)-1,2-diphenylethyl]-2-fluorophenylsulphonamidato-κN]chloro[($\eta^6$)-benzene]ruthenium(II)

[N-[(1R,2R and 1S,2S)-2-(amino-κN)-1,2-diphenylethyl]-4-methoxyphenylsulphonamidato-κN]chloro[($\eta^6$)-benzene]ruthenium(II)

[N-[(1R,2R and 1S,2S)-2-(amino-κN)-1,2-diphenylethyl]-3-methoxyphenylsulphonamidato-κN]chloro[($\eta^6$)-benzene]ruthenium(II)

[N-[(1R,2R and 1S,2S)-2-(amino-κN)-1,2-diphenylethyl]-2-methoxyphenylsulphonamidato-κN]chloro[($\eta^6$)-benzene]ruthenium(II)ato-κN]chloro[($\eta^6$)-benzene]ruthenium(II)

[N-[(1R,2R and 1S,2S)-2-(amino-κN)-1,2-diphenylethyl]-1-naphthylsulphonamidato-κN]chloro[($\eta^6$)-benzene]ruthenium(II)

[N-[(1R,2R and 1S,2S)-2-(amino-κN)-1,2-diphenylethyl]-2-naphthylsulphonamidato-κN]chloro[($\eta^6$)-benzene]ruthenium(II)

[N-[(1R,2R and 1S,2S)-2-(amino-κN)-1,2-diphenylethyl]-pentafluorophenylsulphonamidato-κN]chloro[($\eta^6$)-benzene]ruthenium(II)

[N-[(1R,2R and 1S,2S)-2-(amino-κN)-1,2-diphenylethyl]-methanesulphonamidato-κN]chloro[($\eta^6$)-benzene]ruthenium(II)

[N-[(1R,2R and 1S,2S)-2-(amino-κN)-1,2-diphenylethyl]-trifluoromethanesulphonamidato-κN]chloro[($\eta^6$)-benzene]ruthenium(II)

[N-[(1R,2R and 1S,2S)-2-(amino-κN)-cyclohexyl]-p-tolylsulphonamidato-κN]chloro-[($\eta^6$)-benzene]ruthenium(II)

[N-[(1R,2R and 1S,2S)-2-(amino-κN)-cyclohexyl]-m-tolylsulphonamidato-κN]-chloro[($\eta^6$)-benzene]ruthenium(II)

[N-[(1R,2R and 1S,2S)-2-(amino-κN)-cyclohexyl]-phenylsulphonamidato-κN]-chloro[($\eta^6$)-benzene]ruthenium(II)

[N-[(1R,2R and 1S,2S)-2-(amino-κN)-cyclohexyl]-4-ethylphenylsulphonamidato-κN]-chloro[($\eta^6$)-benzene]ruthenium(II)

[N-[(1R,2R and 1S,2S)-2-(amino-κN)-cyclohexyl]-2,4,6-trimethylphenylsulphonamidato-κN]chloro[(η⁶)-benzene]ruthenium(II)
[N-[(1R,2R and 1S,2S)-2-(amino-κN)-cyclohexyl]-4-chlorophenylsulphonamidato-κN]chloro[(η⁶)-benzene]ruthenium(II)
[N-[(1R,2R and 1S,2S)-2-(amino-κN)-cyclohexyl]-3-chlorophenylsulphonamidato-κN]chloro[(η⁶)-benzene]ruthenium(II)
[N-[(1R,2R and 1S,2S)-2-(amino-κN)-cyclohexyl]-4-fluorophenylsulphonamidato-κN]chloro[(η⁶)-benzene]ruthenium(II)
[N-[(1R,2R and 1S,2S)-2-(amino-κN)-cyclohexyl]-3-fluorophenylsulphonamidato-κN]chloro[(η⁶)-benzene]ruthenium(II)
[N-[(1R,2R and 1S,2S)-2-(amino-κN)-cyclohexyl]-4-methoxyphenylsulphonamidato-κN]chloro[(η⁶)-benzene]ruthenium(II)
[N-[(1R,2R and 1S,2S)-2-(amino-κN)-cyclohexyl]-3-methoxyphenylsulphonamidato-κN]chloro[(η⁶)-benzene]ruthenium(II)
[N-[(1R,2R and 1S,2S)-2-(amino-κN)-cyclohexyl]-1-naphthylsulphonamidato-κN]-chloro[(η⁶)-benzene]ruthenium(II)
[N-[(1R,2R and 1S,2S)-2-(amino-κN)-cyclohexyl]-2-naphthylsulphonamidato-κN]-chloro[(η⁶)-benzene]ruthenium(II)
[N-[(1R,2R and 1S,2S)-2-(amino-κN)-cyclohexyl]-methanesulphonamidato-κN]-chloro[(η⁶)-benzene]ruthenium(II)
[N-[(1R,2R and 1S,2S)-2-(amino-κN)-cyclohexyl]-trifluoromethanesulphonamidato-κN]chloro[(η⁶)-benzene]ruthenium(II)
[N-[(1R,2R and 1S,2S)-2-(amino-κN)-cyclohexyl]-p-tolylsulphonamidato-κN]chloro-[(η⁶)-cumene]ruthenium(II)
[N-[(1R,2R and 1S,2S)-2-(amino-κN)-cyclohexyl]-m-tolylsulphonamidato-κN]-chloro[(η⁶)-cumene]ruthenium(II)
[N-[(1R,2R and 1S,2S)-2-(amino-κN)-cyclohexyl]-phenylsulphonamidato-κN]-chloro[(η⁶)-cumene]ruthenium(II)
[N-[(1R,2R and 1S,2S)-2-(amino-κN)-cyclohexyl]-4-ethylphenylsulphonamidato-κN]-chloro[(η⁶)-cumene]ruthenium(II)
[N-[(1R,2R and 1S,2S)-2-(amino-κN)-cyclohexyl]-2,4,6-trimethylphenylsulphonamidato-κN]chloro[(η⁶)-cumene]ruthenium(II)
[N-[(1R,2R and 1S,2S)-2-(amino-κN)-cyclohexyl]-4-chlorophenylsulphonamidato-κN]chloro[(η⁶)-cumene]ruthenium(II)
[N-[(1R,2R and 1S,2S)-2-(amino-κN)-cyclohexyl]-3-chlorophenylsulphonamidato-κN]chloro[(η⁶)-cumene]ruthenium(II)
[N-[(1R,2R and 1S,2S)-2-(amino-κN)-cyclohexyl]-4-fluorophenylsulphonamidato-κN]chloro[(η⁶)-cumene]ruthenium(II)
[N-[(1R,2R and 1S,2S)-2-(amino-κN)-cyclohexyl]-3-fluorophenylsulphonamidato-κN]-chloro[(η⁶)-cumene]ruthenium(II)
[N-[(1R,2R and 1S,2S)-2-(amino-κN)-cyclohexyl]-4-methoxyphenylsulphonamidato-κN]chloro[(η⁶)-cumene]ruthenium(II)
[N-[(1R,2R and 1S,2S)-2-(amino-κN)-cyclohexyl]-3-methoxyphenylsulphonamidato-κN]chloro[(η⁶)-cumene]ruthenium(II)
[N-[(1R,2R and 1S,2S)-2-(amino-κN)-cyclohexyl]-1-naphthylsulphonamidato-κN]-chloro[(η⁶)-cumene]ruthenium(II)
[N-[(1R,2R and 1S,2S)-2-(amino-κN)-cyclohexyl]-2-naphthylsulphonamidato-κN]-chloro[(η⁶)-cumene]ruthenium(II)
[N-[(1R,2R and 1S,2S)-2-(amino-κN)-cyclohexyl]-methanesulphonamidato-κN]-chloro[(η⁶)-cumene]ruthenium(II)
[N-[(1R,2R and 1S,2S)-2-(amino-κN)-cyclohexyl]-trifluoromethanesulphonamidato-κN]chloro[(η⁶)-cumene]ruthenium(II)
[N-[(1R,2R and 1S,2S)-2-(amino-κN)-cyclohexyl]-p-tolylsulphonamidato-κN]chloro-[(η⁶)-1,3,5-trimethylbenzene]ruthenium(II)
[N-[(1R,2R and 1S,2S)-2-(amino-κN)-cyclohexyl]-m-tolylsulphonamidato-κN]-chloro[(η⁶)-1,3,5-trimethylbenzene]ruthenium(II)
[N-[(1R,2R and 1S,2S)-2-(amino-κN)-cyclohexyl]-phenylsulphonamidato-κN]-chloro[(η⁶)-1,3,5-trimethylbenzene]ruthenium(II)
[N-[(1R,2R and 1S,2S)-2-(amino-κN)-cyclohexyl]-4-ethylphenylsulphonamidato-κN]-chloro[(η⁶)-1,3,5-trimethylbenzene]ruthenium(II)
[N-[(1R,2R and 1S,2S)-2-(amino-κN)-cyclohexyl]-2,4,6-trimethylphenylsulphonamidato-κN]chloro[(η⁶)-1,3,5-trimethylbenzene]ruthenium(II)
[N-[(1R,2R and 1S,2S)-2-(amino-κN)-cyclohexyl]-4-chlorophenylsulphonamidato-κN]chloro[(η⁶)-1,3,5-trimethylbenzene]ruthenium(II)
[N-[(1R,2R and 1S,2S)-2-(amino-κN)-cyclohexyl]-3-chlorophenylsulphonamidato-κN]chloro[(η⁶)-1,3,5-trimethylbenzene]ruthenium(II)
[N-[(1R,2R and 1S,2S)-2-(amino-κN)-cyclohexyl]-4-fluorophenylsulphonamidato-κN]chloro[(η⁶)-1,3,5-trimethylbenzene]ruthenium(II)
[N-[(1R,2R and 1S,2S)-2-(amino-κN)-cyclohexyl]-3-fluorophenylsulphonamidato-κN]-chloro[(η⁶)-1,3,5-trimethylbenzene]ruthenium(II)
[N-[(1R,2R and 1S,2S)-2-(amino-κN)-cyclohexyl]-4-methoxyphenylsulphonamidato-κN]chloro[(η⁶)-1,3,5-trimethylbenzene]ruthenium(II)
[N-[(1R,2R and 1S,2S)-2-(amino-κN)-cyclohexyl]-3-methoxyphenylsulphonamidato-κN]chloro[(η⁶)-1,3,5-trimethylbenzene]ruthenium(II)
[N-[(1R,2R and 1S,2S)-2-(amino-κN)-cyclohexyl]-1-naphthylsulphonamidato-κN]-chloro[(η⁶)-1,3,5-trimethylbenzene]ruthenium(II)
[N-[(1R,2R and 1S,2S)-2-(amino-κN)-cyclohexyl]-2-naphthylsulphonamidato-κN]-chloro[(η⁶)-1,3,5-trimethylbenzene]ruthenium(II)
[N-[(1R,2R and 1S,2S)-2-(amino-κN)-cyclohexyl]-methanesulphonamidato-κN]-chloro[(η⁶)-1,3,5-trimethylbenzene]ruthenium(II) and
[N-[(1R,2R and 1S,2S)-2-(amino-κN)-cyclohexyl]-trifluoromethanesulphonamidato-κN]chloro[(η⁶)-1,3,5-trimethylbenzene]ruthenium(II).

Particularly preferred catalysts for step a) are those which comprise ruthenium complexes which are obtainable by reacting S,S— or R,R—N-p-toluenesulphonyl-1,2-diphenylethylenediamine and (cumene)dichlororuthenium dimer.

In ii), operation is effected in the presence of at least one amine, preferably one amine, at least some of which is present in protonated form.

Also formic acid, formates or mixtures thereof are used for ii).

Preference is given to using mixtures of formic acid with amines. In this way, the corresponding ammonium formates are at least partially formed which can be used in a similar manner.

Useful amines are in particular those of the formula (XV)

$$NR^{10}R^{11}R^{12} \quad (XV)$$

where $R^{10}$, $R^{11}$ and $R^{12}$ are each independently hydrogen, $C_1$-$C_8$-alkyl or benzyl.

Particularly preferred amines are ammonia and those of the formula (XV) where $R^{10}$, $R^{11}$ and $R^{12}$ are each independently $C_1$-$C_8$-alkyl or benzyl.

Particularly preferred amines are those of the formula (XV) where $R^{10}$, $R^{11}$ and $R^{12}$ are each identically ethyl, n-butyl or n-hexyl, although even greater preference is given to the use of triethylamine.

The molar ratio of formic acid to tertiary amine may be, for example, 1:1 to 3:1, and preference is given to a ratio of 1.01:1 to 1.5:1.

The molar ratio of formic acid based on substrate used may be, for example, 1:1 to 3:1, and preference is given to 1:1 to 1.5:1, particular preference to 1.02:1 to 1.1:1.

According to iii), step a) may be carried out in the presence or absence, preferably in the presence, of organic solvents.

Examples of suitable organic solvents include:

amides, for example dimethylformamide, N-methylpyrrolidinone, optionally halogenated aliphatic or araliphatic solvents having up to 16 carbon atoms, for example toluene, o-, m- and p-xylene, chloroform, dichloromethane, chlorobenzene, the isomeric dichlorobenzenes, fluorobenzene, nitriles, for example acetonitrile, benzonitrile, dimethyl sulphoxide or mixtures thereof.

Preferred solvents are acetonitrile, N-methylpyrrolidinone, chloroform, dichloromethane, chlorobenzene, the isomeric dichlorobenzenes, fluorobenzene or mixtures thereof, and particular preference is given to dichloromethane, acetonitrile, N-methylpyrrolidinone or mixtures thereof.

The reaction temperature may be, for example, −10 to 150° C., and preference is given to 20 to 100° C., particular preference to 20 to 80° C.

The reaction times are, for example, between 0.5 h and 48 h, preferably between 6 and 24 h.

The molar amount of ruthenium may be, for example, 0.01 to 1.0 mol %, based on the substrate used, and preference is given to 0.02 to 0.2 mol %, very particular preference to 0.02 to 0.1 mol %.

It is advantageous, although not obligatory, to carry out the reaction in a substantially oxygen-free atmosphere. Substantially oxygen-free means, for example, a content of 0 to 1% by volume, preferably 0 to 0.1% by volume, of oxygen.

The reaction may be accelerated by removing carbon dioxide which is released during the reaction. Advantageous, and therefore encompassed by the invention, is intensive stirring of the reaction mixture at an average stirrer speed of, for example, 100 to 3 000 $min^{-1}$, preferably 500 to 1 500 $min^{-1}$. Alternatively, or supplementarily thereto, the removal of carbon dioxide may be supported by passing an inert gas stream through or over the reaction mixture. Examples of suitable gases include nitrogen, noble gases, for example argon, or mixtures thereof.

A particularly preferred embodiment of step a) is described hereinbelow, although without imposing any limitation.

In a stirred tank, a 1:1 mixture (molar) of formic acid and triethylamine is prepared by simple mixing and compounds of the formula (II) or compounds of the formula (IV) are added in equimolar amounts or in a slight deficiency to this biphasic mixture. Depending on the solubility of the substrate, an amount of an organic solvent is added. The mixture is inertized by passing through nitrogen and the mixture is heated to the desired reaction temperature with vigorous stirring.

The catalyst is added to this mixture as solution in dichloromethane in molar ratios relative to the substrate of, for example, 1:500 to 1:5000, and the reaction mixture is stirred for the desired time. The conversion is followed chromatographically.

The reaction mixture may subsequently be worked up by processes known to those skilled in the art. It has proven advantageous to work up the reaction mixture by adding solvents and dilute aqueous hydrochloric acid or water. After phase separation, the product may be isolated in a manner known per se from the organic phase either distillatively or by a suitable crystallization process.

In step a), enantiomerically enriched compounds of the formulae (III) or (V) are obtained with the definitions and areas of preference specified above.

Depending on the choice of the configuration of the ligands, the S- or R-configured products are obtainable, and the configuration information relates to the carbon atom adjacent to the Ar radical.

The compounds of the formulae (III) or (V) may be isolated or further reacted directly. For intermediate isolation, the reaction mixture may be separated, for example, between water and an organic solvent of low water miscibility, and the desired product transferred to the organic phase. After the removal of the organic solvent, a crude product is obtained which may be purified, for example, by crystallization or distillation.

When compounds of the formula (II) have been used for step a), enantiomerically enriched compounds of the formula (III) are obtained which are reacted in step b) with amines of the formula (VI) and having the definitions and areas of preference specified there.

This may be effected, for example, in such a way that the enantiomerically enriched compounds of the formula (III) are reacted with the amines of the formula (VI), optionally in a solvent. An overview of the synthesis of carboxamides from carboxylic acids, carboxylic esters, carboxylic anhydrides and other carboxamides can be found in Houben-Weyl, 4th edition, volume E 5, 941-1010.

In the case of liquid and gaseous amines, the use of solutions of the amines is suitable. For example, in the case of methylamine, solutions of methylamine in water, methanol or in ethanol may advantageously be used for the reaction of carboxylic esters of the formula (III). For the conversion of free carboxylic acids of the formula (III) to the amides of the formula (V), examples of suitable reactions are those of amines of the general formula (VI) in the presence of coupling reagents such as 2-halopyridinium or -1,3-thiazolium salts, or in the presence of acidic cation exchangers.

It is also possible to convert a compound of the formula (V) to a preferred compound of the formula (V). This may be effected, for example, by transamidation, N-alkylation or N-dealkylation.

In step b), enantiomerically enriched compounds of the formula (V) are then obtained from enantiomerically enriched compounds of the formula (III).

The scope of the invention also encompasses the following compounds of the formula (V):

(S)-3-Hydroxy-3-(2-thiophen-yl)-N-methylpropionamide,
(R)-3-hydroxy -3-(2-thiophen-yl)-N-methylpropionamide,
and any desired mixtures of these compounds, for example the racemate.

Particular mention is made of (S)-3-hydroxy-3-(2-thiophen-yl)-N-methylpropionamide.

The enantiomerically enriched compounds of the formula (V) may then be reduced to the enantiomerically enriched compounds of the formula (I). The reduction of carboxamides to the corresponding amines is known in principle and illustrated by way of summary in Houben Weyl "Methoden der Organischen Chemie", 4th edition, volume E 16 d, 987-1003.

Preference is given to the reaction of compounds of the formula (V) with complex boron or aluminium hydrides, for example lithium aluminium hydride, Red-Al® (sodium bis(2-methoxyethoxy)dihydroaluminate) or sodium borohydride.

Particular preference is given to the reaction of compounds of the formula (V) with lithium aluminium hydride.

Step c) is preferably carried out at temperatures in the range from 0 to 150° C., more preferably in the range from 50 to 110° C. Customarily, the reductions are carried out in ethers as solvents, preferably in cyclic ethers such as tetrahydrofuran or dioxane, or the reductions with Red-Al® can equally be carried out in toluene as solvent.

In the manner according to the invention, the enantiomerically enriched compounds of the formula (I)

where

Ar, $R^1$ and $R^2$ each have the definitions and areas of preference specified above.

Individual compounds of the formula (I) include:

(1S)-3-(methylamino)-1-(2-thiophen-yl)-1-propanol, (1R)-3-(methylamino)-1-(2-thiophen-yl)-1-propanol, (1S)-3-(dimethylamino)-1-(2-thiophen-yl)-1-propanol, (1R)-3-(dimethylamino)-1-(2-thiophen-yl)-1-propanol, (1S)-3-(methylamino)-1-(phenyl)-1-propanol, (1R)-3-(methylamino)-1-(phenyl)-1-propanol, (1S)-3-(methylamino)-1-(4-tolyl)-1-propanol and (1R)-3-(methylamino)-1-(4-tolyl)-1-propanol.

The enantiomerically enriched compounds of the formula (I) which can be prepared according to the invention are suitable in particular for preparing enantiomerically enriched compounds of the formula (XVI)

$$\text{aryl-CH(OR}^{10})\text{—CH}_2\text{—CH}_2\text{NR}^1\text{R}^2 \quad \text{(XVI)}$$

where aryl, $R^1$ and $R^2$ each have the definition and areas of preference specified under the formula (I) and $R^{10}$ is phenyl or naphthyl which may be not at all, singly or multiply substituted by substituents which are each independently selected from the group of cyano, CO—($C_1$-$C_{12}$-alkyl), O—($C_1$-$C_{12}$-alkyl), ($C_1$-$C_{12}$-alkyl), fluorine, chlorine, bromine, $C_1$-$C_{12}$-fluoroalkyl where fluoroalkyl is a singly, multiply or fully fluorine-substituted alkyl radical.

$R^{10}$ is preferably naphthyl.

Preferred compounds of the formula (XVI) are:

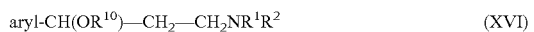

(S)—N-methyl-3-(1-naphthalenyloxy)-3-(2-thienyl)propylamine and (R)—N-methyl-3-(1-naphthalenyloxy)-3-(2-thienyl)propylamine and salts of both and also (S)—Nm-ethyl-3-(4-trifluoromethylphenyloxy)-3-(2-phenyl)propylamine and (R)—N-methyl-3-(4-trifluoromethylphenyloxy)-3-(2-phenyl)propylamine and also mixtures of both (e.g. the racemate) and their salts, and also (S)—N-methyl-3-(2-tolyloxy)-3-(2-phenyl)propylamine and (R)—N-methyl-3-(2-tolyloxy)-3-(2-phenyl)propylamine and also mixtures of both (e.g. the racemate) and their salts, although particular preference is given to (S)—N-methyl-3-(1-naphthalenyloxy)-3-(2-thienyl)propylamine.

The scope of the invention therefore also encompasses a process which, as step d) encompasses the reaction of compounds of the formula (I) with compounds of the formula (XVII) in the presence of a base.

In formula (XVII)

$$R^{10}\text{-Hal} \quad \text{(XVII)}$$

$R^{10}$ has the definition and areas of preference specified under the formula (XVI) and Hal is fluorine, chlorine, bromine or iodine, preferably fluorine.

The compounds of the formula (XVII) used are preferably 1-fluoronaphthalene and 4-chlorobenzotrifluoride.

Useful bases are those which can at least partially deprotonate the compounds of the formula (I) at the alcohol function.

Preferred bases are alkali metal hydroxides and hydrides, for example sodium hydride, optionally with the addition of potassium benzoate or potassium acetate, as described in U.S. Pat. No. 5,362,886, sodium hydroxide and potassium hydroxide.

The compounds of the formulae (I), (V) and (XVI) are suitable in particular for preparing pharmaceuticals, such as preferably serotonin or noradrenaline takeup inhibitors.

The process according to the invention has the advantage that it is possible, starting from reactants which are easily obtainable, to synthesize enantiomerically enriched 1-aryl-3-aminopropanols of the formula (I) and their subsequent products in high overall yields, high enantiomeric excesses and high purities on the industrial scale.

EXAMPLES

Example 1

In a 2 l flask, 180.8 g of sodium methoxide and 1500 ml of toluene were heated to 100° C. and a solution of 257 g of 2-acetylthiophene in 510 ml of dimethyl carbonate was then added dropwise within 4 hours. The methanol formed in the reaction was distilled off as an azeotrope. In a 4 l flask, 120 ml of conc. sulphuric acid in 900 g of ice was initially charged and the cooled reaction mixture was added in such a way that 40° C. was not exceeded. Stirring was continued and the pH was adjusted to pH 1. The phases were separated and the organic phase was extracted three times with aqueous sodium sulphate solution and then concentrated under reduced pressure. The vacuum distillation of the crude product delivered 278 g of methyl β-oxo-(2-thiophene)propionate as a transparent, light yellow liquid (98% pure by GC, 74% of theory).

Example 2

Methyl (3S)-3-hydroxy-3-(2-thienyl)propanoate

In a Schlenk vessel, the catalyst solution is prepared by weighing 314 mg (2.03 equiv.) of S,S-TsDPEN and 263 mg of [(cumene)RuCl$_2$]$_2$ in 10 ml of CH$_2$Cl$_2$ and also admixing with 0.3 ml (2 equiv.) of Et$_3$N and stirring this mixture at room temperature for 15 min.

In a 1 l multinecked flask equipped with a sparging stirrer, reflux condenser and internal thermometer, an HCOOH/Et$_3$N mixture (molar ratio 1:1) is prepared by gradually adding 41 ml of HCOOH dropwise within 20 min to 152 ml of Et$_3$N with stirring and ice cooling. 190 g of methyl 2-oxo-3-(2-thienyl)propionate are added to this biphasic mixture, the homogeneous yellow solution is admixed with 0.1 l of dichloromethane and the entire mixture is degassed by passing through argon for 20 min. It is heated to 36° C. and the dark red catalyst solution is added all at once to the reaction mixture with vigorous stirring. Stirring is effected at 800 rpm while passing argon through the reaction mixture for 14 h.

After diluting with 0.3 l of 1N HCl and 0.3 l of $CH_2Cl_2$ and phase separation, the $H_2O$ phase is extracted 2× more with $CH_2Cl_2$, the combined organic phases are washed with 150 ml of NaCl solution, dried over $MgSO_4$, filtered and the solvent is removed. The crude product is used without purification in the next stage 100% conversion.

The conversion and enantiomer analysis were effected by gas chromatography on an HP gas chromatograph using an IVADEX capillary column (12.5 m, 0.3 µm layer thickness using individual temperature programmes).

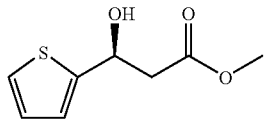

$^1$H NMR (d1-chloroform, 400 MHz): δ=7.23 (m, 1H, Ar—H), 6.95 (m, 2H, Ar—H), 5.36 (dd, 1H, CHOH), 3.71 (s, 3H, $OCH_3$), 2.86 (m, 2H, CHH) ppm.

$^{13}$C NMR (d1-chloroform, 100 MHz): δ=185.3 (C=O), 146.8 (C, Ar), 127.1 (CH, Ar), 125.3 (CH, Ar), 124.1 (CH, Ar), 66.9 (CHOH), 52.4 (CH3), 43.5 (CH2) ppm.

Chiral GC: 14.05, 14.41 min. ee=98.2%.

Example 3

115 g of methyl (3S)-3-hydroxy-3-(2-thienyl)propanoate are initially charged and admixed with 618 ml of a 2 molar methanolic methylamine solution. This mixture is stirred at 60° C. for 4 h, cooled and then concentrated under reduced pressure. In this way, 118 g of N-methyl-(3S)-3-hydroxy-3-(2-thienyl)propanamide (purity 86%; 88% of theory) are obtained. The crude product may be used in the next stage or else recrystallized from methylene chloride and hexane. This delivered 93 g of N-methyl-(3S)-3-hydroxy-3-(2-thienyl) propanamide (76% of theory) as white crystals. As an alternative, the purification may also be done by distillation.

The conversion and enantiomer analysis were effected by gas chromatography on an HP gas chromatograph using an IVADEX capillary column (12.5 m, 0.3 µm layer thickness using individual temperature programmes).

Example 4

1728 ml of dry tetrahydrofuran are initially charged with 52 g of lithium aluminium hydride and heated to reflux. At the same time, dropwise addition of 86.4 g of N-methyl-(3S)-3-hydroxy-3-(2-thienyl)propanamide dissolved in 692 g of tetrahydrofuran is commenced. Once dropwise addition is complete, stirring is continued under reflux overnight. The reaction mixture is then cooled to room temperature and 1037 ml of water are cautiously added dropwise. 173 ml of a 10% sodium hydroxide solution were then added dropwise and the solution was filtered. The solvent was removed under reduced pressure. The crude solution was admixed with 346 ml of 1 N sodium hydroxide solution extracted 3 times with 345 ml of toluene each time. The organic phases are combined and the volatile constituents are removed under reduced pressure to obtain 76 g of (1S)-3-(methylamino)-1-(2-thienyl)-1-propanol (84% purity, 80% of theory).

The invention claimed is:

1. A method for preparing a 3-hydroxy-3-(2-thienyl)propionamide compound of the formula:

wherein
Ar represents 2-thiophenyl, which is optionally monosubstituted or polysubstituted by fluoro, nitro, hydroxyl, $C_{1-12}$-alkyl, $C_{1-12}$-haloalkyl, $C_{5-14}$-aryl and $C_{1-8}$-alkoxy; and
$R_1$ and $R_2$ are each independently hydrogen, $C_{1-20}$-alkyl, $C_{4-14}$-aryl or $C_{5-15}$-arylalkyl;
said process comprising reducing the compound of the formula:

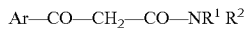

wherein
Ar, $R^1$ and $R^2$ are as defined above; in the presence of a catalyst constituted from a ruthenium-containing compound of the formula:

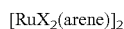

wherein
X is chlorine, bromine or iodine; and
arene is a coordinated compound having 6 to 12 ring carbon atoms, which may be further substituted by up to 6 radicals, each of which is independently selected from the group consisting of $C_{1-8}$-alkyl, benzyl and phenyl; and a compound of the formula:

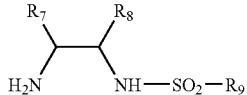

wherein
$R^7$ and $R^8$ are each independently $C_{1-20}$-alkyl, $C_{4-15}$-aryl or $C_{5-16}$-arylalkyl, or $R^7$ and $R^8$ together are a straight-chain or branched $C_{3-12}$-alkylene radical; and
$R^9$ is $C_1$-$C_{20}$-alkyl, $C_1$-$C_{20}$-fluoroalkyl or $C_4$-$C_{15}$-aryl.

2. The method according to claim 1, wherein $R^9$ represents $C_1$-$C_{20}$-alkyl or $C_4$-$C_{15}$-aryl.

3. The method according to claim 1, which is carried out in the presence of a hydrogen-transferring compound.

4. The method according to claim 3, wherein the hydrogen-transferring compound is selected from the group consisting of formic acid and isopropanol.

5. A method for preparing a 3-hydroxy-3-(2-thienyl)propionamide compound of the formula:

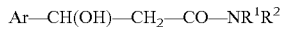

wherein
Ar represents 2-thiophenyl, which is optionally monosubstituted or polysubstituted by fluoro, nitro, hydroxyl, $C_{1-12}$-alkyl, $C_{1-12}$-haloalkyl, $C_{5-14}$-aryl and $C_{1-8}$-alkoxy; and
$R^1$ and $R^2$ are each independently hydrogen, $C_{1-20}$-alkyl, $C_{4-14}$-aryl or $C_{5-15}$-arylalkyl;
said process comprising:
a) reducing the compound of the formula:

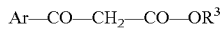

wherein

Ar is as defined above; and $R^3$ represents hydrogen, $C_{1-20}$-alkyl, $C_{4-14}$-aryl or $C_{5-15}$-arylalkyl;

in the presence of a catalyst constituted from a ruthenium-containing compound of the formula:

[RuX$_2$(arene)]$_2$ wherein

X is chlorine, bromine or iodine; and arene is a coordinated compound having 6 to 12 ring carbon atoms, which may be further substituted by up to 6 radicals, each of which is independently selected from the group consisting of $C_{1-8}$-alkyl, benzyl and phenyl;

and a compound of the formula:

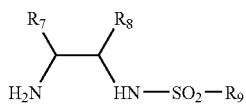

wherein $R^7$ and $R^8$ are each independently $C_{1-20}$-alkyl, $C_{4-15}$-aryl or $C_{5-16}$-arylalkyl, or $R^7$ and $R^8$ together are a straight-chain or branched $C_{3-12}$-alkylene radical; and $R^9$ is $C_1$-$C_{20}$-alkyl, $C_1$-$C_{20}$-fluoroalkyl or $C_4$-$C_{15}$-aryl;

to form the resulting compound of the formula:

Ar—CH(OH)—CH$_2$—CO—OR$^3$ and then b) reacting said resulting compound with an amine of the formula:

HNR$^1$R$^2$ wherein

R$^1$ R$^2$ have the meanings given above.

6. The method according to claim 5, wherein $R^9$ represents $C_1$-$C_{20}$-alkyl or $C_4$-$C_{15}$-aryl.

7. The method according to claim 5, which is carried out in the presence of a hydrogen-transferring compound.

8. The method according to claim 7, wherein the hydrogen-transferring compound is selected from the group consisting of formic acid and isopropanol.

* * * * *